(12) United States Patent
Smither (10) Patent No.: US 7,943,906 B2
(45) Date of Patent: May 17, 2011

(54) HIGH SPATIAL RESOLUTION X-RAY AND GAMMA RAY IMAGING SYSTEM USING DIFFRACTION CRYSTALS (75) Inventor: Robert K. Smither, Hinsdale, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 166 days.

(21) Appl. No.: 12/272,483

(22) Filed: Nov. 17, 2008

(65) Prior Publication Data

US 2009/0225945 A1    Sep. 10, 2009

Related U.S. Application Data (63) Continuation-in-part of application No. 11/479,797, filed on Jun. 30, 2006, now Pat. No. 7,468,516.

(60) Provisional application No. 61/105,339, filed on Oct. 14, 2008.

(51) Int. Cl.
G21K 1/02 (2006.01)
(52) U.S. Cl. .................................................. 250/363.1
(58) Field of Classification Search ............. 250/363.02, 250/363.04, 363.1, 370.09
See application file for complete search history.

(56) References Cited

U.S. PATENT DOCUMENTS

5,869,841 A    2/1999    Smither

*Primary Examiner* — David P Porta
*Assistant Examiner* — Mark R Gaworecki
(74) *Attorney, Agent, or Firm* — Cherskov & Flaynik

(57) ABSTRACT

A method and a device for high spatial resolution imaging of a plurality of sources of x-ray and gamma-ray radiation are provided. The device comprises a plurality of arrays, with each array comprising a plurality of elements comprising a first collimator, a diffracting crystal, a second collimator, and a detector.

20 Claims, 11 Drawing Sheets

HIGH SPATIAL RESOLUTION X-RAY AND GAMMA RAY IMAGING SYSTEM USING DIFFRACTION CRYSTALS

CROSS REFERENCE TO RELATED APPLICATIONS

This application is based upon and claims the benefit of U.S. provisional application No. 61/105,339, entitled "HIGH SPATIAL RESOLUTION X-RAY AND GAMMA RAY IMAGING SYSTEM USING DIFFRACTION CRYSTALS", filed Oct. 14, 2008 by Robert K. Smither, the entire disclosure of which is herein specifically incorporated by reference for all that it discloses and teaches. This application is a continuation in part of U.S. patent application Ser. No. 11/479,797 entitled HIGH RESOLUTION X-RAY AND GAMMA RAY IMAGING USING DIFFRACTION LENSES WITH MECHANICALLY BENT CRYSTALS filed Jun. 30, 2006, Robert K. Smither, all of which is incorporated herein by reference.

CONTRACTUAL ORIGIN OF INVENTION

The United States Government has rights to this invention pursuant to Contract No. DE-AC02-06CH11357 between the U.S. Department of Energy and the University of Chicago, representing Argonne National Laboratory.

BACKGROUND OF THE INVENTION

1. Field of the Invention

This invention relates to a method for improving imaging of a source of radiation and to a device for imaging a source of radiation, and more specifically, this invention relates to a method and device for producing a high spatial resolution three-dimensional image of a source of x-ray and gamma-ray radiation for medical and other application by using a plurality of diffracting crystals, collimators, and detection devices.

2. Background of the Invention

Cancer tumor cells have high rates of metabolism and multiply rapidly. Substances injected into the body tend to migrate to locations of such high growth and become incorporated in this new growth. If the injected substance incorporates a short-lived radioactive isotope, the location of a tumor can be detected by locating the region of high radioactivity. Aside from pinpointing tumor location, an image of the tumor is also desirable to ascertain its shape, size, and juxtaposition with adjacent structures. For many medical applications it is imperative that a tumor be detected as early as possible, and early tumors are very small in size. Thus their detection and identification requires the ability to image very small sources. Also, medical research often uses small animals, with very small organs, and the availability of devices with very high spatial resolution is of the utmost importance.

One method used to detect tumors is to first inject a body with a biological substance that contains radioactive compounds such as the Technetium isotope $^{99m}Tc$, which is a 140.5 kiloelectronVolt (keV) gamma emitter having a half-life of 5.9 hours. The gamma rays are detected by a large sodium iodide (NaI) scintillator crystal placed behind a collimator grid yielding at best an 8 millimeter (mm) resolution at the location of the source. The scintillator is viewed by a plurality of photomultiplier tubes and the location of a scintillation event is determined by a computer analysis of the relative intensity of the photomultiplier signals. The collimator/scintillator assembly is placed above and very close to the patient. Aside from this method yielding a low resolution of between approximately 8 mm and 1 centimeter (cm), the image produced is limited to the plane parallel to the surface of the scintillator. As such, the technique provides no depth information about the source. This deficiency can be remedied somewhat by adding another collimator/scintillator assembly below the patient, comparing the counting rate of the two scintillators, and thus estimating the position of the source along the line joining them. In the latest revision of this method the large NaI detector plus collimator is rotated around the patient, taking a plurality of images at different angles. This allows one to generate a three-dimensional image of the radiation emitting area. There are considerable additional costs associated with this method and the fact that this method has been introduced in spite of the additional costs underscores the importance of three-dimensional imaging.

Another popular imaging technique is positron emission tomography (PET), used in diagnosis and medical research. In PET, a chemical compound containing a short-lived, positron-emitting radioisotope is injected into the body. The positrons (positively charged beta particles) are emitted as the isotope decays. These particles annihilate with electrons in surrounding tissue. Each annihilation simultaneously produces two 511 (keV) gamma rays traveling in opposite directions. After passing through collimators, these two gamma rays are detected simultaneously by scintillation detectors placed at 180 degrees to each other, and on opposite sides of the patient. The signals from the detectors' photomultiplier tubes are analyzed by a computer to facilitate the production of an image of the radiation-emitting region.

Numerous drawbacks exist with scintillation detector tomography. For instance, the typical coarse resolution of no less than 8 mm often results in smaller structures being overlooked. This prevents early detection of cancerous tumors when they are least likely to have metastasized and when treatment is most likely to succeed. This is especially a disadvantage in the detection of breast cancer tumors wherein the tumors often become virulent before growing to a detectable size. Presently, mammography uses x-rays to detect tissue calcification. The assumption is made that this calcification is due to dead cancer cells and that there is a live cancer tumor in the immediate vicinity. Often however, there is no live tumor where calcification has been detected. In fact, the calcification may not have been due to a tumor at all. Unfortunately then, positive mammography results often lead to unnecessary surgical operations.

Also, because poor spacial resolution often causes images of actual small tumors to be diffuse, variations in background radiation are often mistaken for actual tumors, leading to unnecessary surgical operations. This inadvertent incorporation of background radiation is an artifact of scintillation detector use wherein the detector must be large enough to cover a given area of the body. Aside from intercepting the radiation emanating from the source under observation, however, the large detectors also detect all ambient background radiation penetrating the scintillating region and this ambient radiation is analyzed as if it had been emitted by the source under observation.

Another drawback to using imaging techniques incorporating scintillation detectors is that all of the various radiations emitted by the source are detected by the detectors. As such, a specific radiation having an energy indicative of a specific, injected isotope cannot be easily scrutinized.

Recently, efforts have been made to improve scintillation detector tomography. Some PET instruments now achieve a resolution as small as 4 mm. Such improvements entail considerable expenditures and have the additional drawback that the improvement in resolution has come at the cost of a decrease in counting rate. This entails in turn either a longer examination time per patient or the injection of a stronger dose of radiation. Furthermore, the prospects for further improvements in resolution are limited by the fact that such improvements require collimators with ever smaller apertures, and therefore greater mass, together with lower count rates. This increase in collimator mass will increase the number of forward Compton-scattered photons in the collimators and these forward scattered photons are often indistinguishable from those emanating directly from the source.

Significant improvements in spatial resolution and in detection efficiency as well as a three dimensional location of the source using a crystal diffraction method for focusing the radiation emanating from the source was disclosed in U.S. Pat. No. 5,869,841 (1999) (granted to the same inventor as the present invention and assigned to the same assignee) and incorporated herein by reference. The enhanced focusing provided in the '841 patent allows the use of much smaller amounts of radioactive substances in order to locate features of interest in the patient. Experiments at the inventor's laboratory have demonstrated the effectiveness of this method and have achieved a spatial resolution of 7 mm. While this is adequate under many circumstances, better spatial resolution would provide significant advantages.

Thus a need exists in the art for an improved method and device for imaging x-ray and gamma-ray sources with sufficient spacial resolution to accurately observe structures smaller than 7 mm in size, even down to 1 mm in size or less. The invented method and the resulting device must have sufficient energy resolution to allow the imaging of radiation of a selected energy to the exclusion of others. The method and device also must limit the radiation to which the patient is exposed by incorporating a redirecting mechanism to detect radiation emanating from a tumor while disregarding ambient levels of radiation.

SUMMARY OF THE INVENTION

It is an object of the present invention to provide a method and a device for high spatial resolution imaging sources of gamma-ray and x-ray radiation that overcome many of the disadvantages of the prior art.

Another object of the present invention is to provide a device for improved spatial resolution in the imaging of sources of gamma and x-ray radiation emanating from a subject. A feature of the present invention is the use of an array comprising a plurality of collimator-crystal-collimator-detector elements, each element comprising a source collimator to direct radiation emanating from a narrow region of space onto a diffracting crystal and of a detector collimator to direct onto a detector radiation diffracted by that crystal. An advantage of the invention is the generation of a high-resolution image of the source while the subject is under examination.

A further object of the present invention is to provide a device for improved spatial resolution in three-dimensional imaging of sources of gamma and x-ray radiation emanating from a subject. A feature of the present invention is the use of a plurality of non-coplanar assemblies each comprising a plurality of collimator-crystal-collimator-detector elements to record data simultaneously for analysis by a computer. An advantage of the invention is the rapid generation of a two- or three-dimensional image of the source while the subject is under examination.

Still another object of the present invention is to provide a method for producing a high-resolution image of a small radiation source which is located in a patient. A feature of the invention is the use of high purity and high quality diffracting crystals 1 mm wide or less. An advantage of the invention is the imaging of millimeter size sources into images of comparable size. Another advantage of the invention is the obviation of unnecessary, invasive surgical procedures to locate a tumor.

Yet another object of the present invention is to provide a radiation imaging method having a fast imaging time. A feature of the invention is using scintillation detectors to locate the approximate position of the radiation source and then the use of a high efficiency crystal diffraction system to produce a high-resolution image of the source that can be viewed by a multi-element detector array. An advantage of the invented method compared to typical pure scintillation detector methods is that the amount of radiation necessary to produce a high-resolution image is relatively small, with a one micro-Curie source producing an image in three minutes.

Another object of the present invention is to provide a radiation imaging method wherein there is a sharp one to one correspondence between source location and image location. A feature of the invention is the use of narrow (1 mm or less) collimators between the sources and the diffracting crystals and between these crystals and the detectors. Another feature of the invention is the use of arrays of small size detectors (1 mm or less) to image the radiation. An advantage of the invented method is a sharp image of the radiating source as recorded by the detectors.

Yet another object of the present invention is to provide a three-dimensional imaging device. A feature of the invention is the use of a plurality of movable detector arrays. An advantage of the invention is that a detailed three-dimensional image of a source can be obtained quickly, with a small amount of radiation, and at low cost.

Another object of the present invention is to provide an economical and manageable imaging device. A feature of the invention is that each of its detector arrays comprises a plurality of thin, long, and arcuately bent individually mounted crystal units. An advantage of the invention is that a detector array can be built rapidly and that a defective crystal in one element of the array can be replaced quickly and at low cost.

Still another object of the present invention is to allow the imaging system to observe radiation of a selected energy to the exclusion of other energies. A feature of the present invention is that the angle at which a crystal diffracts radiation depends very sensitively on the energy of the radiation. An advantage of the present invention is that the array can be so constructed as to select only radiation of the desired energy.

In brief, the present invention provides a method for high spatial resolution imaging of one or more sources of x-ray and gamma-ray radiation comprising: locating the sources of radiation proximally to a point (this point preselected as a reference point); supplying a plurality of elements, each element comprising a first collimator, defined by a pair of first plates, wherein the first collimator is adapted to direct radiation emanating from locations proximal to the point; a diffracting crystal adapted to receive and diffract the radiation directed by the first collimator; a second collimator defined by a pair of second plates, wherein the second collimator is adapted to direct radiation diffracted by the diffracting crystal; and a detector adapted to detect the radiation directed by the second collimator; supplying a means for analyzing said detected radiation to collect data as to the type and location of the source of the radiation; and supplying a means for converting the data to an image.

The present invention also provides a device for high spatial resolution imaging of one or more sources of x-ray and gamma-ray radiation comprising: a means for locating the sources of radiation proximally to a point; a plurality of elements each element comprising a first collimator, defined by a pair of first plates, wherein the first collimator is adapted to direct radiation emanating from locations proximal to the point; a diffracting crystal adapted to receive and diffract the radiation directed by the first collimator; a second collimator defined by a pair of second plates, wherein the second collimator is adapted to direct radiation diffracted by the diffracting crystal; and a detector adapted to detect the radiation directed by the second collimator; the device also comprising a means for analyzing said detected radiation to collect data as to the type and location of the source of the radiation and a means for converting the data to an image.

The invented method can be further enhanced by using diffracting crystals bent in an arcuate shape, a multi-element collimator-crystal-collimator-detector array, and a plurality of such multi-element collimator-crystal-collimator-detector arrays.

BRIEF DESCRIPTION OF THE DRAWING

The present invention together with the above and other objects and advantages may best be understood from the following detailed description of the embodiment of the invention illustrated in the drawing, wherein.

DETAILED DESCRIPTION OF THE INVENTION

The present invention utilizes the phenomenon of crystal diffraction for gamma- or x-rays, wherein there is a unique correspondence between the energy of the photons incident upon a crystal and the angle at which they are diffracted. In the 'Bragg diffraction' case the photons are diffracted near the surface while in the 'Laue diffraction' case the photons are diffracted in the interior of the crystal, but in both cases the diffraction phenomenon is a volume effect that depends upon the internal structure of the crystal. Both categories of diffraction can re-focus the diffracted beam. Both Bragg and Laue diffraction are discussed in detail in previously referenced U.S. Pat. No. 5,869,841.

For both Laue and Bragg diffraction, diffraction occurs only when the Bragg condition is obeyed, (equation 1):

$$\lambda = 2d_{hkl} \sin p \qquad (1)$$

where $\lambda$ is the radiation wavelength, p the angle between the direction of the radiation beam and the atomic layers with which the radiation interacts, and $d_{hkl}$ the spacing between these atomic layers from which are indicated by the Miller indices h, k, l, (one can convert energy E in keV to wavelength $\lambda$ in Angstrom units by using the relation $\lambda = 12.397/E$).

Performance of the invented device depends on two properties of the diffracting crystals: acceptance angle and diffraction efficiency. With perfectly parallel atomic layers, only rays within a few arc seconds of p will be diffracted (i.e., the "acceptance angle" is only a few seconds of arc), so that one can obtain a large diffraction efficiency only if the rays are nearly parallel, i.e. only if the source is very far away.

Acceptance Angle Detail

This parallel-ray problem is avoided by increasing the acceptance angle. The acceptance angle controls the solid angle for diffraction at a single wavelength by the crystal and thus the sensitivity of the imaging system. It also controls the range of energies that can be diffracted by the crystal at any one angle. The acceptance angle in bent crystals is controlled by the length of the crystal in the direction of the photon trajectory and by the radius of curvature of the bent crystal. Atomic mass absorption in the crystal limits the size of the crystal one can use.

Figure 1A:
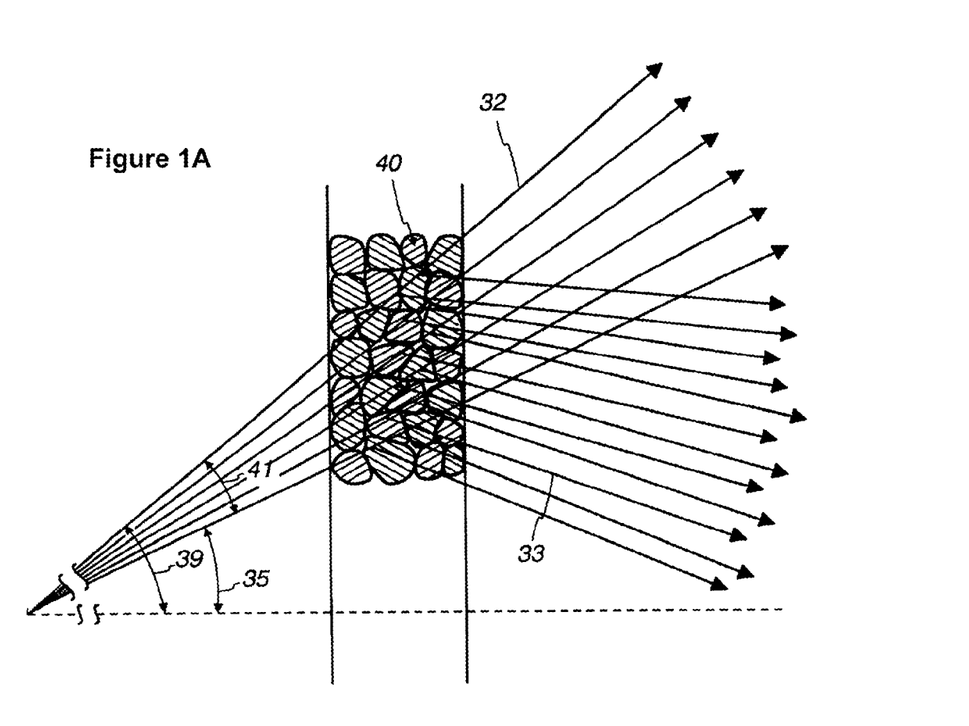
FIG. 1A shows the effect on Laue diffraction if imperfections are either naturally present or else artificially introduced within a diffracting crystal, in accordance with features of the present invention.

FIG. 1A shows the effect of a mosaic structure for Laue diffraction. If imperfections are either naturally present or else artificially introduced within the crystal so that all the crystal planes are no longer parallel to each other, rays coming at different angles 39 will still find planes 40 for which the Bragg condition is obeyed. As seen in FIG. 1A, the imperfections in the crystal give rise to a three dimensional mosaic structure. The angle 41 between the rays 35 having the lowest angle p and those 39 having the largest p is the acceptance angle, also known as the "rocking angle." Ordinarily, rocking angles of between 200 and 800 arc seconds are employed. This is adequate for a first scan where a spatial resolution of 4 mm suffices. A rocking angle of between 50 and 150 seconds of arc is required when a 1 mm spatial resolution is required. Thus the degree of imperfection can be tailored to obtain the desired acceptance angle.

Figure 1B:
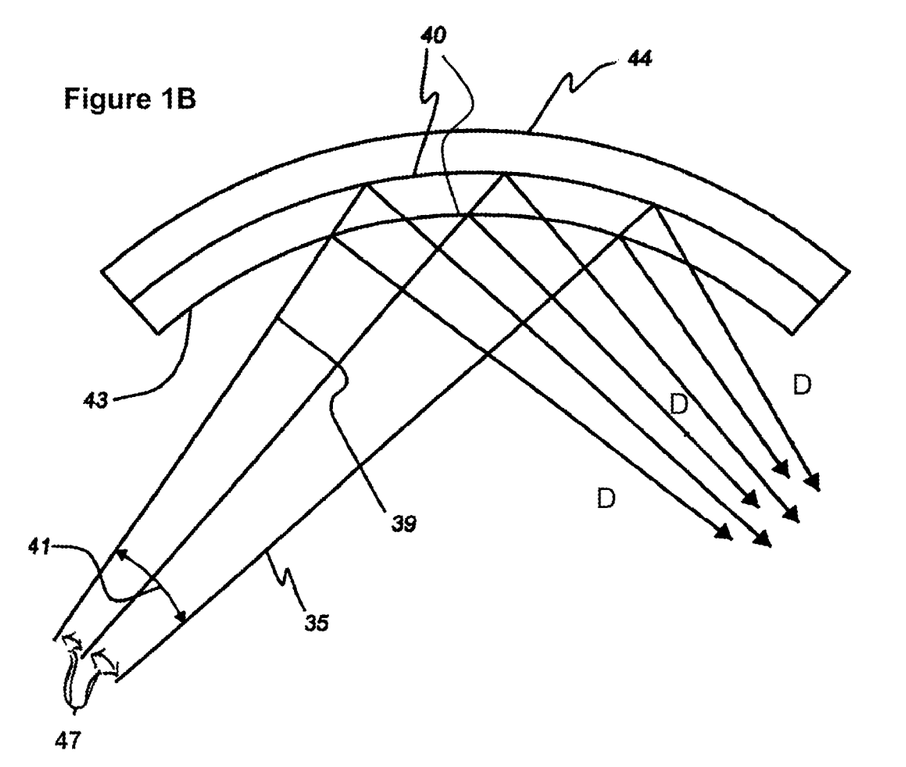
FIG. 1B illustrates the effect of crystal bending in Bragg Diffraction, in accordance with features of the present invention.

FIG. 1B shows that for Bragg diffraction the acceptance angle 41 can be increased if the crystal is curved toward the direction "D" of the radiation beam. Rays coming at different angles 47 will still find planes 40 for which the Bragg condition will be obeyed. The angle 41 between the rays 35 with the lowest angle p and the rays 39 with the largest p is the acceptance angle. The curved shape of the crystals produces a significant focusing effect. The highest degree of focusing for Bragg diffraction occurs when the radius of curvature is equal to L/sin p, where L is the distance from the source to the crystal. Performance with Bragg diffraction is improved as one reduces imperfections and impurities in the crystals.

Advantages of Bent Crystals

Many different kinds of crystals (bent, unbent, mosaic, etc.) can be used in this invention. The examples used in this discussion are bent crystals of nearly perfect silicon or germanium, where 'nearly perfect' denotes high-grade commercially available silicon or germanium. They produce high quality imaging in many applications. The acceptance angle of the crystal is controlled by the curvature in the crystal. The diffraction efficiency of the crystal also depends somewhat on the curvature of the crystal, but the fact that the diffraction efficiency remains near 100 percent for a large range of curvatures and energies (80 keV to 200 keV), allows one to vary the acceptance angle of the crystal without changing the diffraction efficiency. The properties and advantages of bent diffraction crystals are discussed in detail in U.S. patent application Ser. No. 11/479,797, "High resolution x-ray and gamma ray imaging using diffraction lenses," by the present inventor and assigned to the same assignee, incorporated herein by reference.

The large acceptance angle in a curved crystal is made possible by the fact that the photon travels through the crystal until it encounters a region where the Bragg condition ($\lambda=2d \sin p$) is met, where $\lambda$ is the photon wavelength, d is the spacing between adjacent crystal planes and p is the angle of incidence of the photon on the crystalline planes. At this location the photon is diffracted and, if the crystal curvature is large enough, the photon will not pass through a second region where the Bragg condition is met so it will leave the crystal undeflected. This allows for nearly 100 percent diffraction efficiency. If the curvature is too small, then the photon is partially diffracted back into the original direction. If the curvature is too large then the diffraction efficiency is reduced. In the energy range of 100 keV to 150 keV, the curvature can change by a factor of 20 without affecting the diffraction efficiency by a large mount.

Figure 2A:
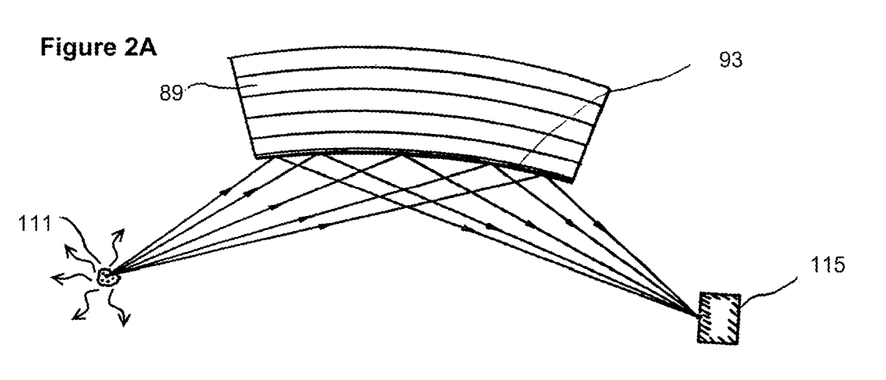
FIG. 2A illustrates the focusing effect of crystal bending in Bragg diffraction, in accordance with features of the present invention.

The classic Bragg focusing geometry is shown in FIG. 2A. This geometry can give a very sharp line focus at a detector 115 for a point source 111. The radius of curvature, R, needed to obtain a sharp focus is given by equation 2, $$R=L/\sin p, \quad (2)$$

wherein L is the distance from the source to the crystal 89 and sin p is the sine of the Bragg angle. Note the heavily accented volume 93 on the front surface of the crystal where the diffraction takes place. This is the case for low energy photons. With high energy photons where mass absorption is low enough so that the photon can penetrate deep into the crystal, this type of focusing can also take place deep inside the crystal. With bent crystals the photon passes through the crystal until it finds the location where the Bragg condition is satisfied and is diffracted. See FIG. 1B. If the curvature is correct, i.e. if equation 2 is obeyed, then focusing occurs. If mass absorption is low enough for the photon to pass through the crystal in the long direction then this type of focusing can take place even when the photon enters the front end of the crystal and leaves through the back of the crystal.

Figure 2B:
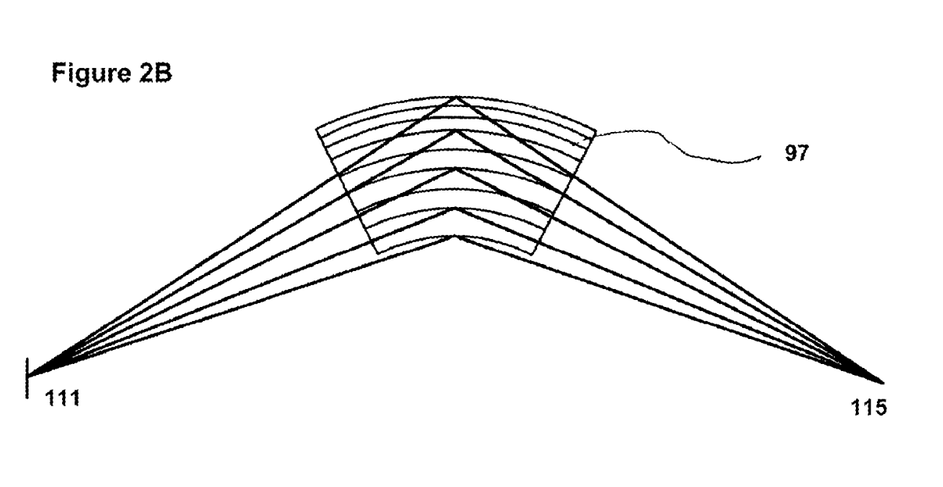
FIG. 2B illustrates the focusing effect of crystal bending in Laue diffraction, in accordance with features of the present invention.

A sharp focus also can be obtained with a Laue diffraction geometry. The Laue focusing geometry is shown in FIG. 2B. The necessary radius of curvature needed for a sharp focus is smaller than in the Bragg geometry (equation 2). It also depends on the set of crystalline planes that has been chosen to provide focusing. Diffraction takes place in a very small volume. Thus the volume 97 depicted in FIG. 2B is a small volume element in a diffracting crystal. This volume is often only a few 10's of microns in all directions. Thus the curvature that counts is only in that volume.

The thickness of the bent crystal affects the focusing properties, the diffraction efficiencies, and the area viewed at any one time. Advantages of this invention are that one can vary the thickness, the curvature, the length, the material, the selection of the crystalline planes and both the distance from the source to the crystals and the distance from the crystals to the detector and the size and type of detector (pixel, strip, wide or narrow) with considerable independence, to achieve the best results. The depth of focus for good resolution (1 mm or less) can be quite long, 20 cm to 100 cm. For high resolution one will use thin crystals, 2 mm or less. For low resolution and wide coverage one will use thicker crystals.

Crystal Bending Detail

The following steps can be used to provide elastically bent crystals:

a) selecting a crystalline material and cutting from large single crystals single crystal slabs of desired thickness and with Miller indices orientation determined according to the radiation to be focused;

b) forming sets of two or more juxtaposed plates, at least one of which plates is one of said crystal slabs, by contacting said plates with an uniform layer of adhesive placed intermediate the plates, wherein said glue hardens only when it is activated;

c) bending to a predetermined curvature one or more of said sets by means of a bending apparatus that allows in-situ measurements of the curvature of the plates;

d) activating said glue while the set of plates is in the bending apparatus; and e) releasing said set from the bending apparatus.

Typical dimensions for the bent crystal of silicon are: length 1-2 cm, width 5-10 cm (into the plane of the figure and thickness 0.5 mm to 2 mm, bending radius of 20 to 40 meters. Typically, the bent crystal is cemented to a thin backing plate in the curved configuration. The collimators thin plates of lead, tungsten, or other high-atomic-number material.

The Imaging System

Figure 3A:
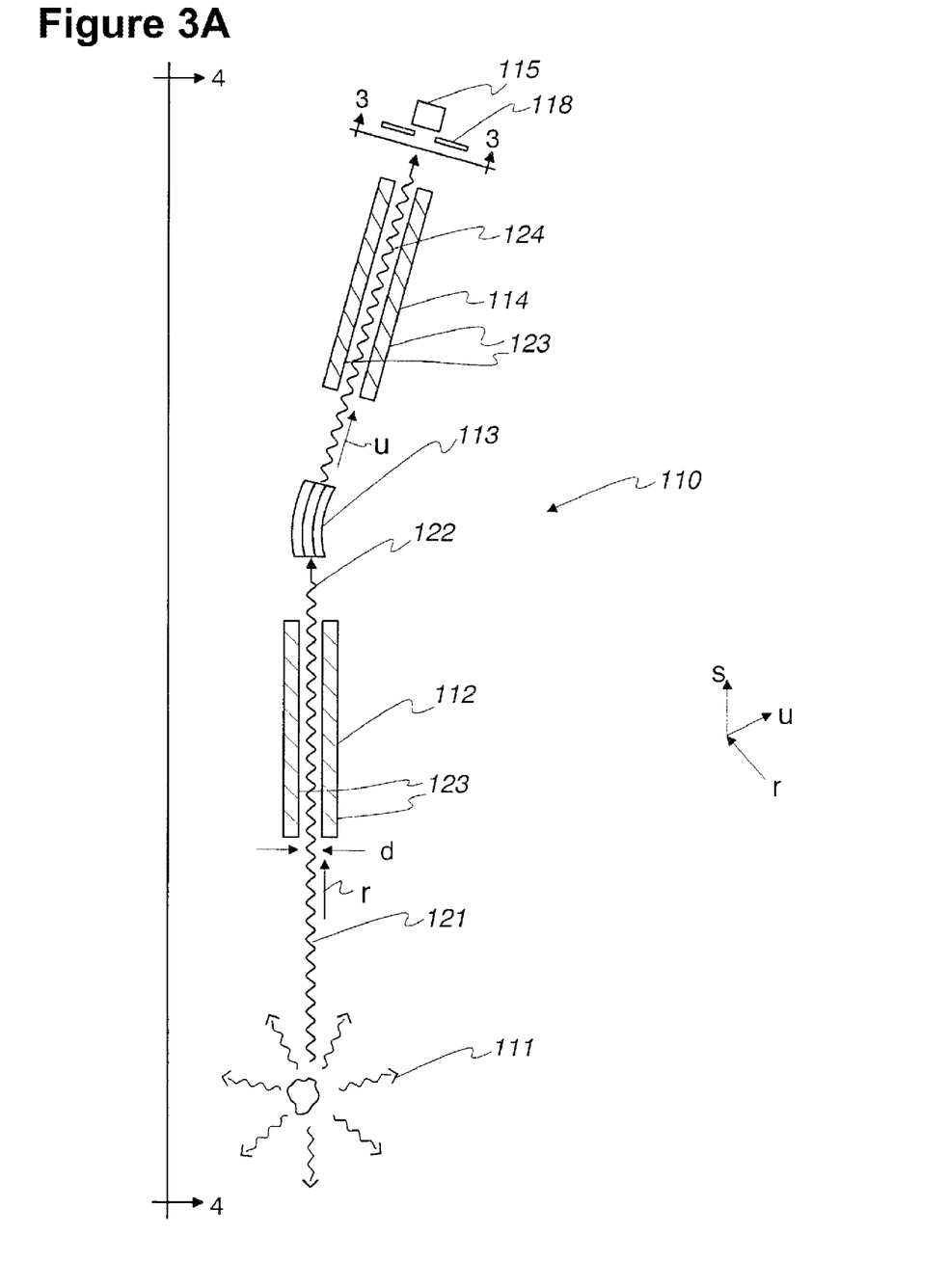
FIG. 3A is a cross-sectional view of a single basic element of the invented imaging system in accordance with features of the present invention.

The present x-ray imaging system comprises one or more arrays each comprising a plurality of basic elements. The basic element 110 of the invented imaging system is shown in FIG. 3A. The radioactive source 111 emits gamma- or x-rays. A beam in a first direction 121 passes through a first or "source" collimator 112. X-rays 122 exiting from the first collimator are diffracted by a crystal 113 to a second direction 124 so as to pass through a second or "detector" collimator 114 and be detected by the detector 115 (FIG. 3A depicts Laue diffraction). In the Laue embodiment of the invention shown in FIG. 3A, the crystal is a bent crystal of silicon. Unbent, mosaic, or segmented crystals can also be used. Typical dimensions for a bent crystal of silicon are: length 1-2 cm, width 5-10 cm (into the plane of the figure) and thickness 0.5 to 2 mm, bending radius of 20 to 50 meters. Spatial resolution can be improved by placing a narrow slit 118 in front of the detector. Typically, the bent crystal is cemented to a thin backing of the same curvature as the crystal. The collimators are made of lead, tungsten, or other high-atomic-number material. Typically the collimators comprise parallel plates 123 separated by a distance d so as to form an elongated slit of width d.

The orientation of the basic element 110 can be specified by a triad of three vectors of unit length: r, directed from the source 111 to the crystal 113 (the direction of photon travel from the source to the crystal); u, from the crystal 113 to the detector 115; and s, the direction of the elongated slit formed by the collimator plates 123 with, in standard vector notation s=u×r (s projects out of the plane of the paper in FIG. 3A).

Figure 3B:
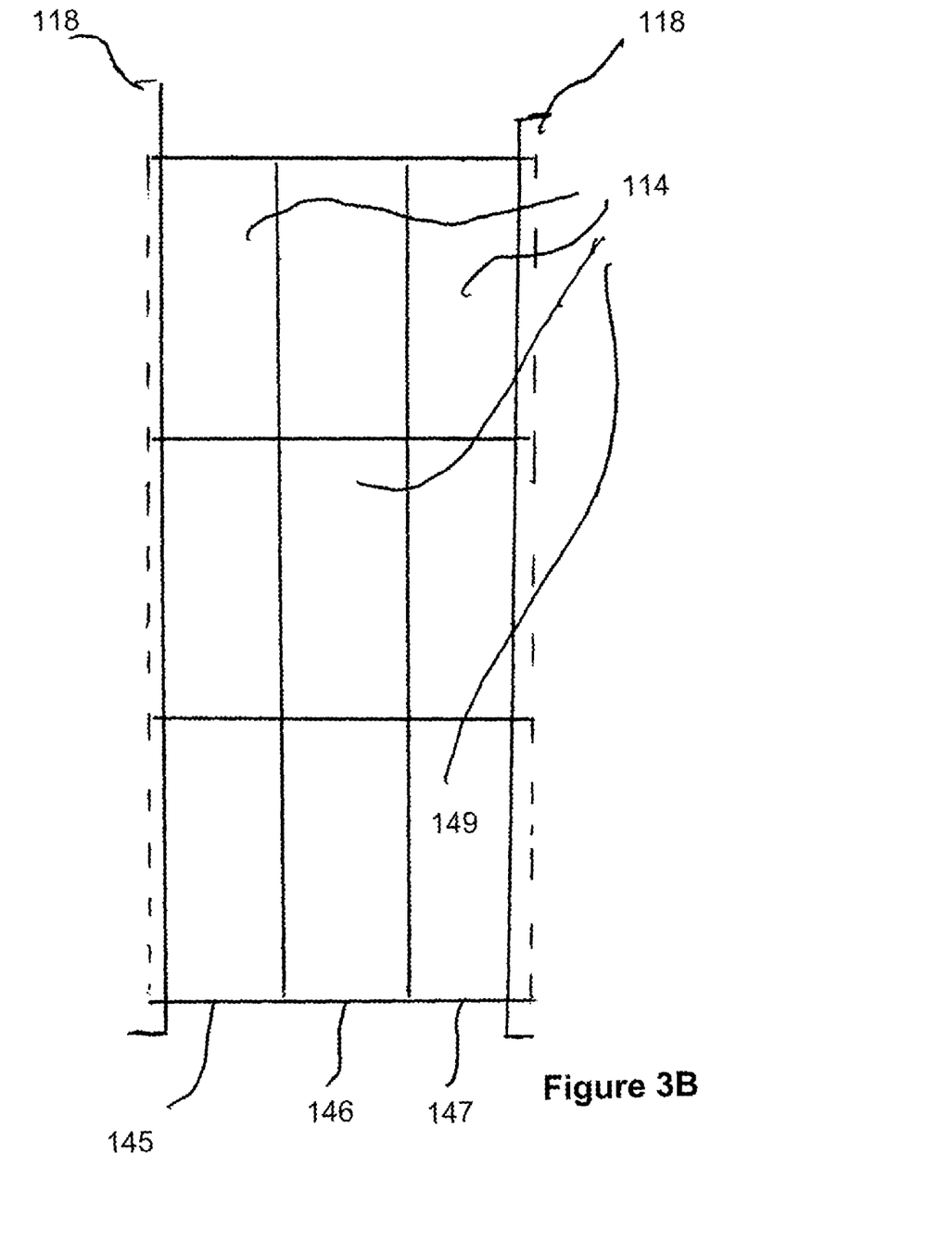
FIG. 3B is a detail view taken along line 3-3 of a detector for the basic element depicted in FIG. 3A, in accordance with features of the present invention.

The detector 115 may comprise an array of photo diodes or a pixel detector similar to that used to record an optical image in a digital camera. A more suitable detector array can be made with a series of cadmium-telluride solid state detectors (CT detectors) or a cadmium-zinc-telluride (CZT detectors). FIG. 3B is a view of FIG. 3A taken along the line 3-3 which depicts three strip CT or CZT detectors 145, 146, 147, each of which comprises a plurality of sections 149. Electric signals from each section 149 is processed by a computer. These detectors made in thin strips and then subdivided in short sections result a long pixel type detector which improves the spatial resolution and reduces background. Also, a substantial fraction of the incident photons lose all their energy in these detectors and the detectors produce voltage pulses proportional to that energy. Then the computer circuitry can select pulses corresponding to photons emitted by the source 111 and exclude those due to ambient background. The width of the strip detector has an affect on the spatial resolution of the system. With a detector strip width of 0.3 mm the measured FWHM (Full Width at Half Maximum) spatial resolution is 0.33 mm.

The use of bent crystals allows many different geometries, including focusing ones where the distance from source to crystal is not equal to the distance from the crystal to the detector. Also the lengths of collimators used to focus the radiation do not have to be equal, provided that no photon straight-line path from the source to the detector exists. It is also not necessary that the crystal curvature be uniform. Rather the curvature needs to vary slowly enough so that the diffraction zone can contain enough scattering centers to diffract the photon efficiently. Crystal materials other than silicon and germanium could be quite useful in this type of imaging system when grown as near perfectly as silicon and germanium. For instance quartz can be used for photon energies below 200 keV and tungsten for photon energies above 200 keV.

In one embodiment of the invention, the lengths and positions of the collimators are such that no straight-line path exists for photons from the source 111 to the detector 115. The viewing angle and thus the angular resolution of the system using the above parameters can be as low as 50 arcsec. This corresponds to a spatial resolution of 0.25 mm FWHM for a source 50 cm from the crystal and 0.5 mm FWHM for a source at 100 cm from the crystal.

Once the curvature is right for Bragg type focusing and the energy of the photon is high enough to penetrate the crystal, then the crystal enables resolutions as low as 0.2 mm FWHM. Bragg type focusing can occur in the Laue geometry as well, resulting in similar high spatial resolution.

Figure 4:
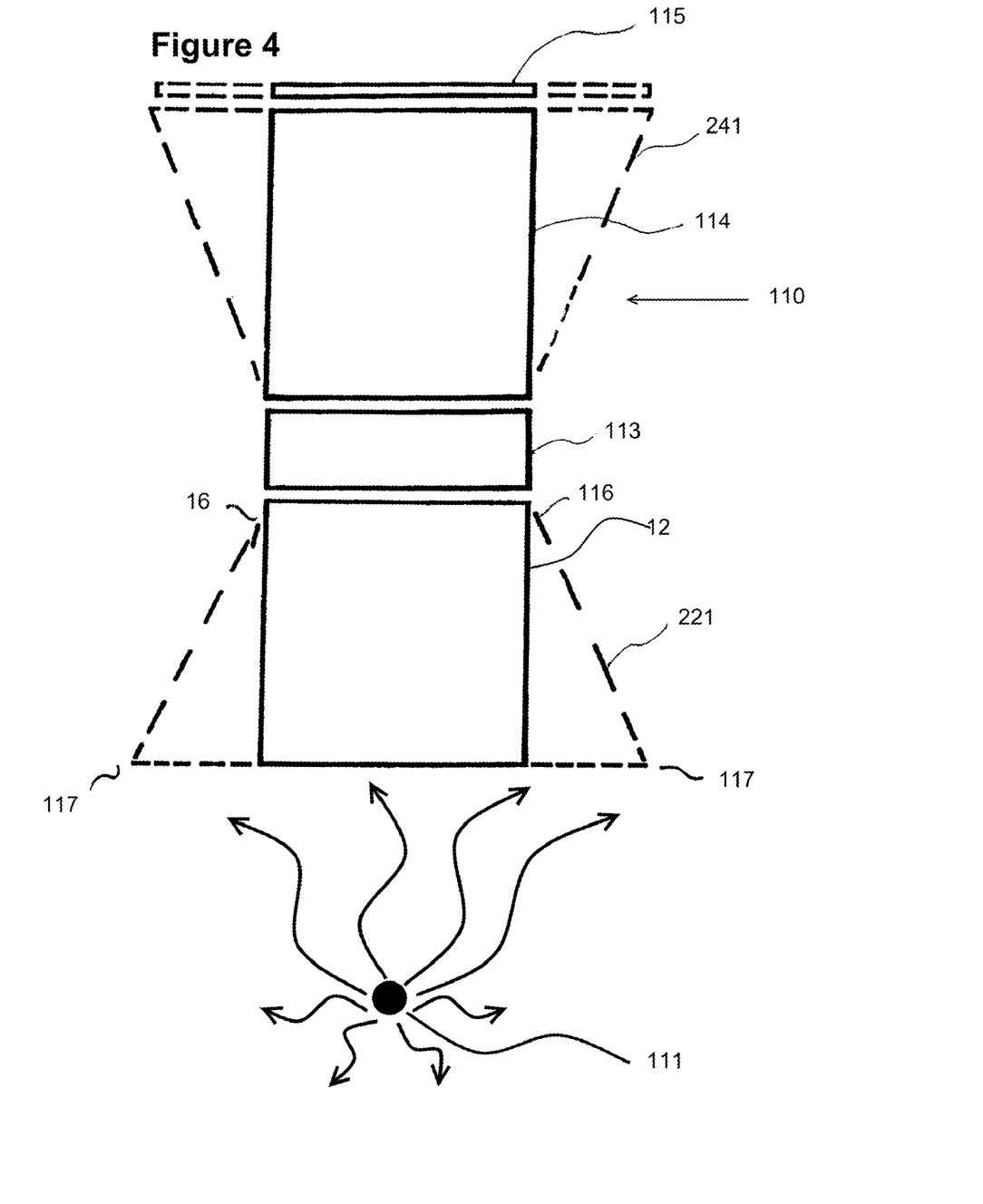
FIG. 4 is a cross plan view of a single basic element of the invented imaging system as shown in FIG. 3, taken along lines 4-4, in accordance with features of the present invention.

FIG. 4 is a view of FIG. 3 taken along the line 4-4 and provides a top view of the collimator-crystal-collimator-detector basic element 110 of FIG. 4. The dashed lines 221 and 241 indicate possible trapezoidal shapes for the collimator plates 123. In the configuration shown, the proximal ends 116 of the collimator plates are positioned medially from the distal crystal ends 117 of the first collimator plates allowing an increased viewing area in a direction perpendicular to the plane formed by the photon travel directions 121 and 124 in FIG. 3. The bent crystals can be seen to function as cylindrical mirrors, imaging a strip area of the source, i.e. a strip perpendicular to the plane of curvature onto a strip of detectors perpendicular to the plane of curvature.

Imaging Arrays

Figure 5A:
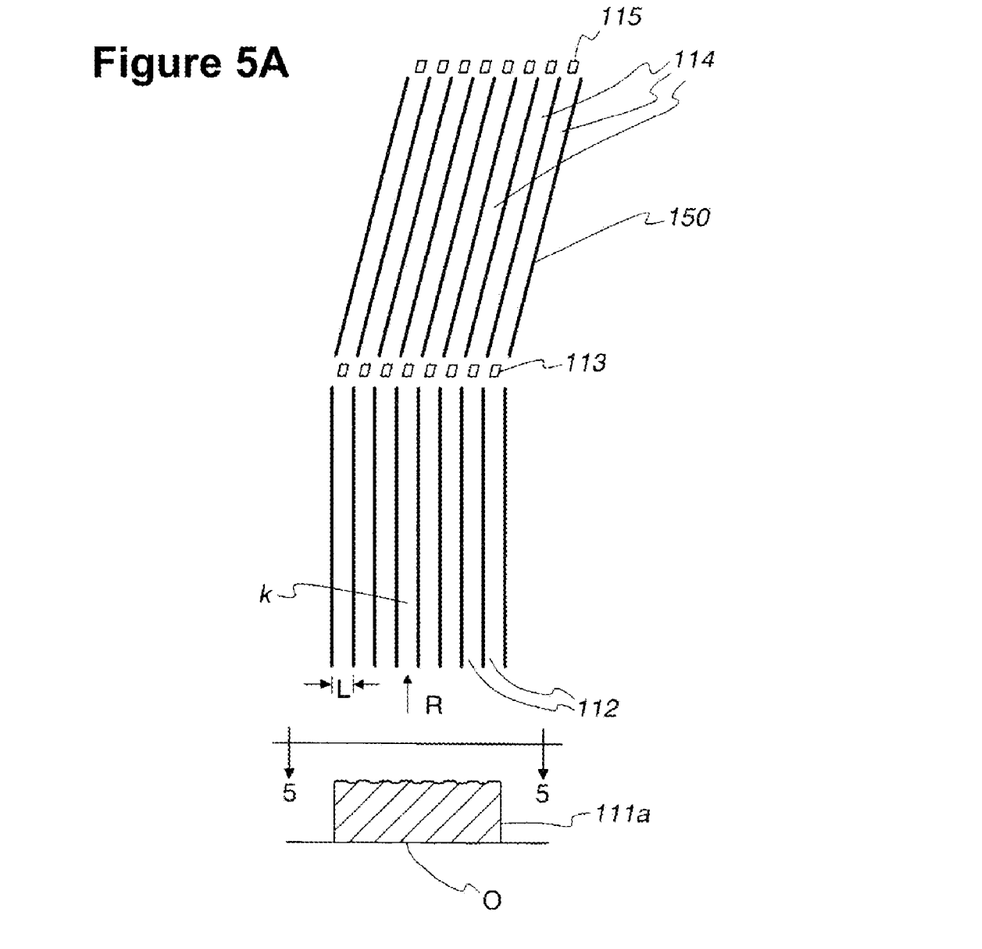
FIG. 5A is a cross sectional view of an imaging array comprising elements shown in FIG. 3, in accordance with features of the present invention.

FIG. 5A shows a first embodiment of an imaging array 150 according to the present invention. The array comprises a plurality of the collimator-crystal-collimator-detector combinations 110 described above, with a distance L between adjacent plates 123. A plurality of collimator-crystal-configurations 110 can be combined so that a large source area is covered by the imaging system. If the system uses mainly the Laue mode of diffraction, then the crystal can be stacked close together. If the system uses the Bragg mode, where diffraction occurs at the surface of the crystal, then a small space must be left between the crystal elements for photons to be able to strike the concave surface of the crystal and then diffract from that surface. Typically the source collimators 112 are coplanar with their plates 123 mounted parallel to each other. Specific collimators will be designated as i,j, .... The collimators have parallel vectors $r_i$, $r_j$, ... that are displaced from each other by the plate separation L. A medially located collimator k has its vector $r_k$ aligned with a point O around which the sources are located. One can define a viewing direction R for the array, where R is aligned with the vector $r_i$ for the array. Similarly, vectors $s_i$, $s_j$, ... designating the direction of the slit openings for the collimators are parallel and from these one can define a slit orientation S for the array, where S is a vector that is parallel with $s_i$.

MODE OF OPERATION

Figure 5B:
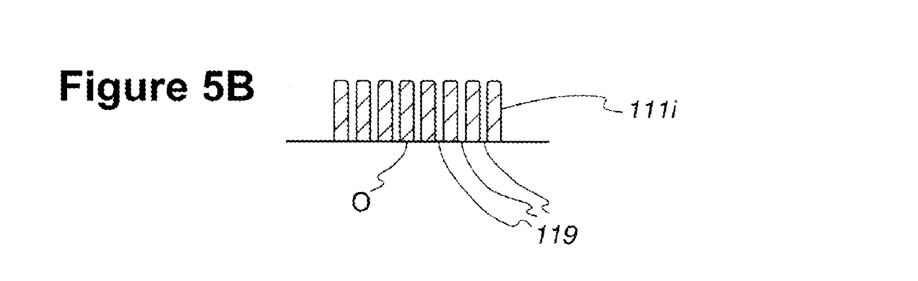
FIG. 5B is a profile view taken along line 5-5 of the image constructed by the imaging array of FIG. 5A, in accordance with features of the present invention.

The crystals 113 are long thin strips and their view of the source area is a long thin strip. The multiple crystal array in FIG. 5A allows one to view a large area of the source 111 a at once, depicted as region 111a ('111 actual'). There are, however, areas in the forms of strips 119 of the source that are not visible at any one time. These are the areas facing the gaps between adjacent crystals. Thus one obtains a striped source image 111i ('111 imaged') if the source is viewed from the line 5-5 in FIG. 5A. This is shown in FIG. 5B. To view the whole source area one must move the imaging system or the object being viewed perpendicular to the direction D. This motion is small, just the spacing between crystal strips which can be as small as 1 mm. Thus the full image can be viewed in a short time.

Figure 6:
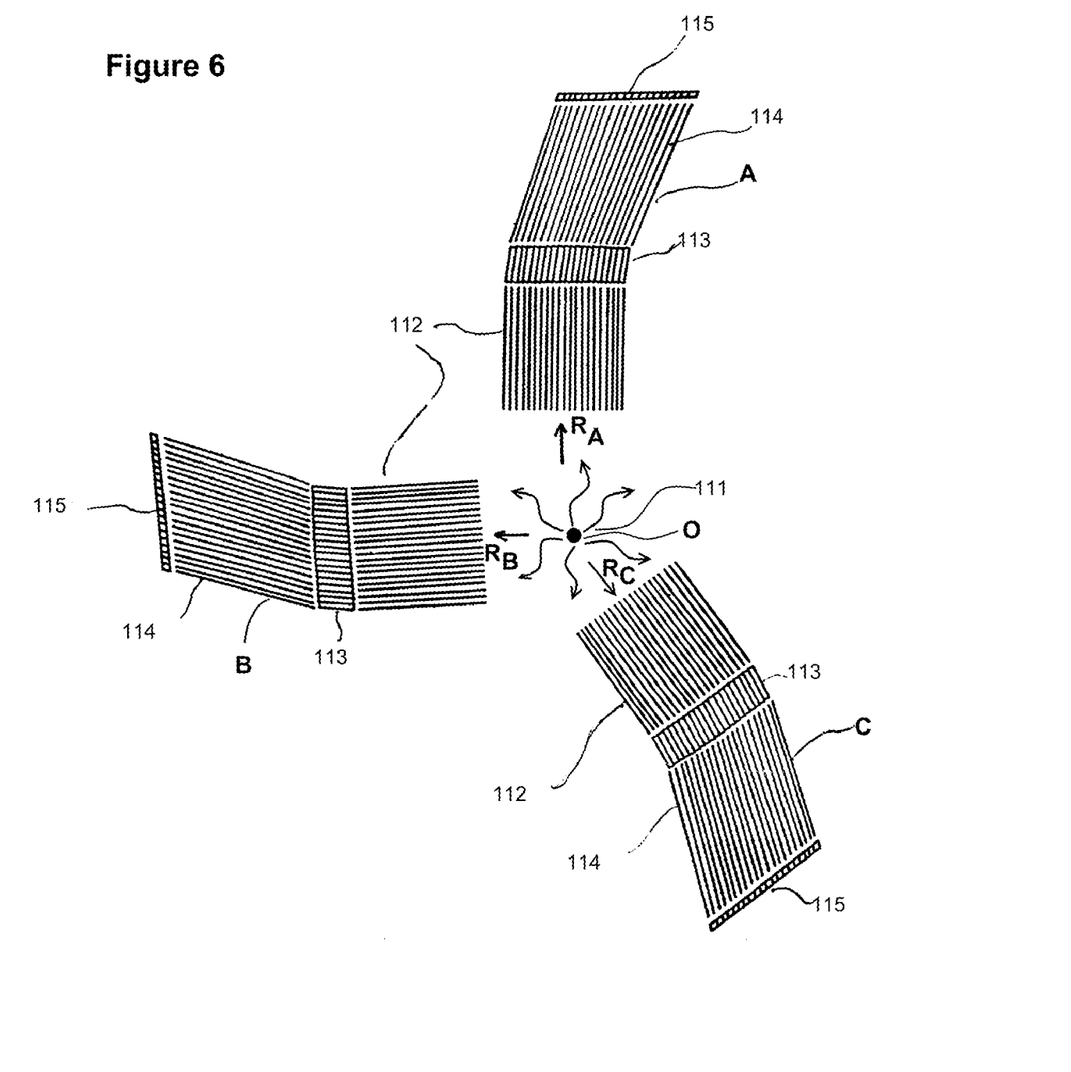
FIG. 6 is a cross sectional view of an imaging system comprising arrays shown in FIG. 5, in accordance with features of the present invention.

To provide a two- or three-dimensional image of a source or sources in a fixed object, a plurality of co-planar non-parallel imaging arrays can be used. In one embodiment shown in FIG. 6, a device having at three co-planar non-parallel imaging arrays A, B, and C, i.e. three co-planar arrays with three non-parallel viewing directions $R_A$, $R_B$, and $R_C$, is used to provide a two-dimensional image of a source 111 ($R_A$ being a vector parallel to $r_{Ai}$, $r_{Aj}$, ... of the collimators in array A, and analogously for $R_B$, and $R_C$. The slit orientation $S_A$, $S_B$, $S_C$ is out of the plane of the paper for all three arrays and the same for all three arrays. The use of three non-parallel viewing direction arrays enables the construction of an unambiguous two-dimensional image of a source under most circumstances. The need for three arrays arises from the fact that there can be more than one source point viewed by an array at any one time. Thus if there are sources at points (x1, y1) and (x2, y2), the detector data from two arrays cannot distinguish between this situation and one where the sources are at points (x1, y2) and (x2, y1). The third array removes this ambiguity. In the alternative, just as one can better depict properties of a 3-dimensional object by rotating the object in front of a camera (or revolving the camera around the object), one can remove the above ambiguity in the location of two sources by relative rotation between the sources and a system of one or two imaging arrays. One may construct a three-dimensional imaging system by using six or more fixed arrays. One suitable arrangement is where the six arrays constitute two intersecting orthogonal planes, with each plane containing three arrays. Also, a three-dimensional imaging system can be constructed with three arrays in a plane and with means to impart motion to the source orthogonally to that plane.

Figure 7:
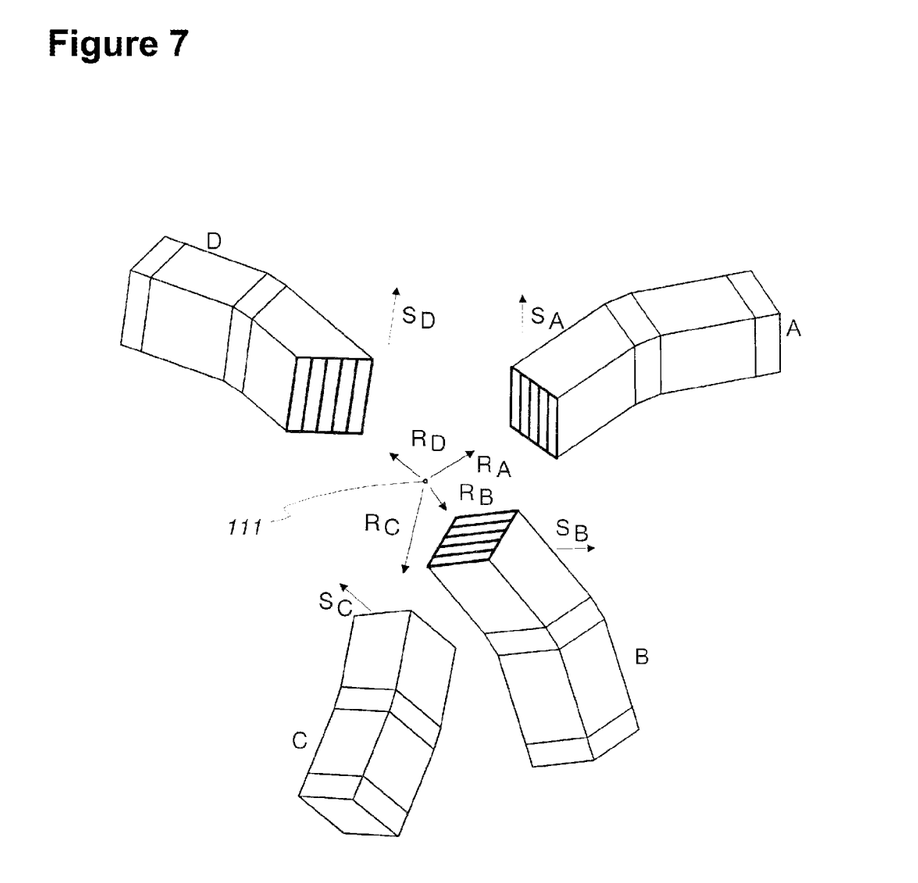
FIG. 7 is a perspective view of an alternative embodiment of an imaging system comprising arrays shown in FIG. 5, in accordance with features of the present invention.

FIG. 7 shows a preferred embodiment with an assembly of four arrays A, B, C, and D in an arrangement that allows imaging of a three-dimensional source. The directions $R_A$, $R_B$, $R_C$ and $R_D$ are such that no more than two lie in the same plane. Moreover, none of the vectors $S_A$, $S_B$, $S_C$ and $S_D$ are parallel to each other. When detectors in specific collimators have detected x-rays is then a simple mathematical procedure to obtain the coordinates of the source points by projecting back from their respective crystals along the r vectors of the collimators. It must be noted that in some specific symmetric cases, some source points may be masked by others. Such masking can be detected by relative translational or rotational motion between the source and the detectors. In an embodiment of the invention, rotation in the plane of the paper of the source with respect to the arrays (or rotation of the arrays with respect to the source) improves the speed with which an image is collected and its quality.

In fact, a single array suffices in an imaging system where the source is rotated around a vertical axis and is also moved vertically. Also, it may prove advantageous to provide means to rotate individual arrays around an axis parallel to the source collimators.

While in general one can obtain imaging of complex source configurations by using merely one array with a combination of lateral and rotational motions, the larger the number of arrays one uses, the smaller the amounts of radiation that must be injected in a patient.

Other Imaging Arrays Using a Similar Approach

Figure 8:
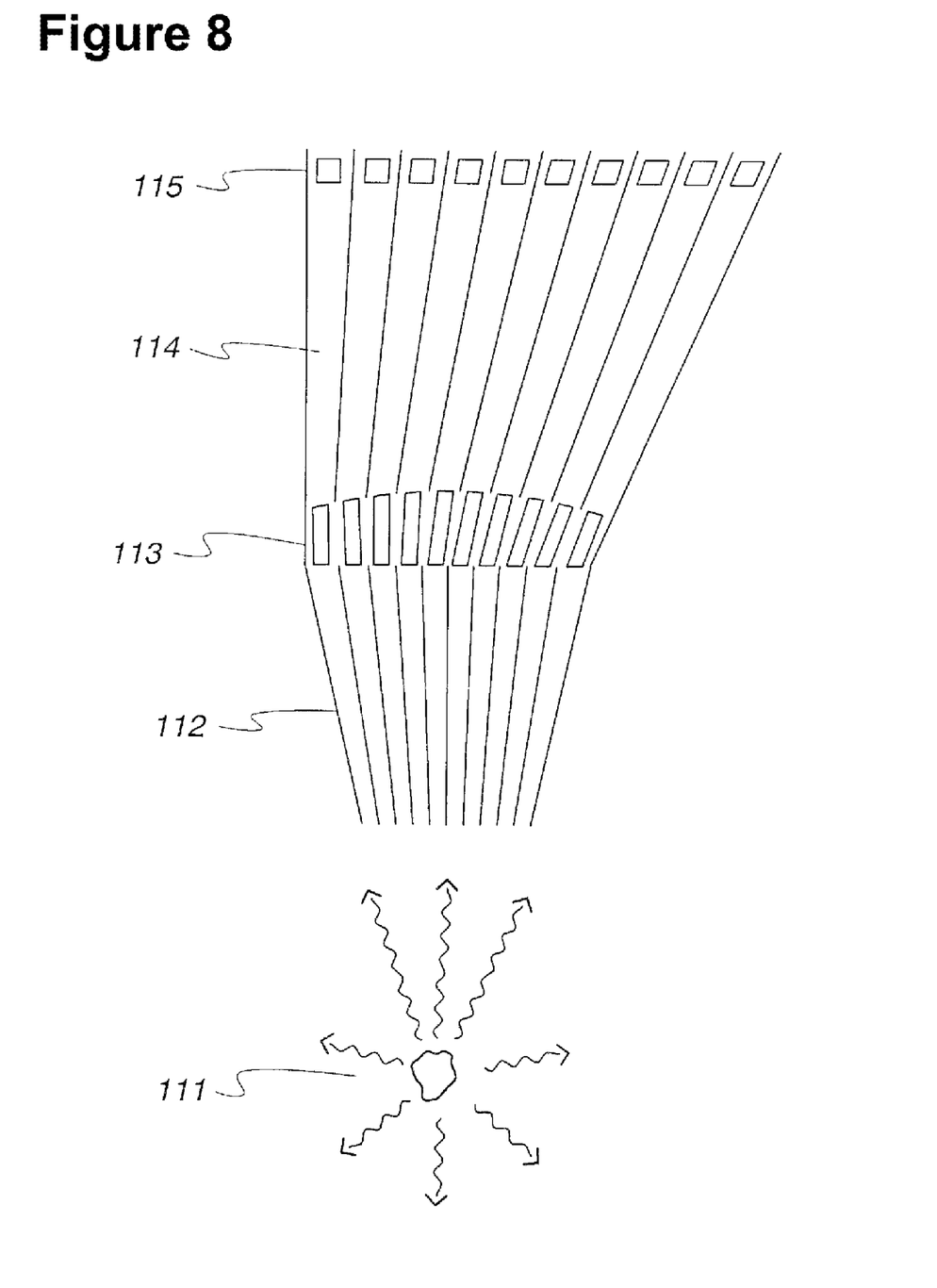
FIG. 8 is a cross sectional view of an alternative embodiment of an imaging array in accordance with features of the present invention.

FIG. 8 shows an alternative embodiment of an imaging array. In this embodiment the source collimators are not parallel but emanate radially from the source so that the crystals view a common source point. The view at that source point is still a strip of the object area and three scanning arrays are still needed to do efficient 2-D imaging but now all the detectors of each array view the same source point. This arrangement enables the detection and imaging of very weak sources, with the imaging being accomplished by relative rectilinear motion of the source with respect to the arrays.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The embodiment of the invention i which an exclusive property or privilege is claimed is defined as follows:

1. A method for high spatial resolution imaging of one or more sources of x-ray and gamma-ray radiation comprising:
a) locating the sources of radiation proximally to a point;
b) supplying a plurality of elements, each element comprising
a first collimator, defined by a pair of first plates, wherein the first collimator is adapted to direct radiation emanating from locations proximal to the point;
a diffracting crystal adapted to receive and diffract the radiation directed by the first collimator;
a second collimator defined by a pair of second plates, wherein the second collimator is adapted to direct radiation diffracted by the diffracting crystal; and
a detector adapted to detect the radiation directed by the second collimator;
c) supplying a means for analyzing said detected radiation to collect data as to the type and location of the source of the radiation; and
d) supplying a means for converting the data to an image.

2. The method as recited in claim 1 wherein said image is produced by an array of elements such that the first plates are parallel to a first line that joins one said crystal to said point.

3. The method as recited in claim 1 further comprising choosing said diffracting crystals from 'high grade' commercially available diffracting crystals and mechanically bending said crystals in an apparatus.

4. The method as recited in claim 1 wherein said method further comprises providing means to impart linear and rotational motion to the sources.

5. The method as recited in claim 1 further comprising positioning said diffracting crystals so as to employ Laue diffraction in diffracting radiation from said sources.

6. The method as recited in claim 1 further comprising positioning said diffracting crystals so as to employ Bragg diffraction in diffracting radiation from said sources.

7. The method as recited in claim 6 further comprising positioning said diffracting crystals so that said crystals act as focusing crystals and said elements have a spatial resolution of 20 arcsec FWHM.

8. The method as recited in claim 1 wherein said image is produced by a plurality of arrays each array comprising one or more of said elements such that the first plates in each array are parallel to a first line first line that joins one said crystal to said point, with said first line being different for each array and with no two said first lines parallel to each other.

9. The method as recited in claim 8 wherein said first plates in each array are perpendicular to a second line with said second line being different for each array, and with no two said second lines parallel to each other.

10. The method as recited in claim 1 wherein said method further comprises providing means to impart linear and rotational motion to the elements.

11. A device for high spatial resolution imaging of one or more sources of x-ray and gamma-ray radiation comprising:
a) a means for locating the sources of radiation proximally to a point;
b) a plurality of elements, each element comprising
a first collimator, defined by a pair of first plates, wherein the first collimator is adapted to direct radiation emanating from locations proximal to the point;
a diffracting crystal adapted to receive and diffract the radiation directed by the first collimator;
a second collimator defined by a pair of second plates, wherein the second collimator is adapted to direct radiation diffracted by the diffracting crystal; and
a detector adapted to detect the radiation directed by the second collimator;
c) means for analyzing said detected radiation to collect data as to the type and location of the source of the radiation; and d) a means for converting the data to an image.

12. The device as recited in claim 11 further comprising means to impart linear and rotational motion to the sources.

13. The device as recited in claim 11 further comprising means to impart linear and rotational motion to the elements.

14. The device as recited in claim 11 wherein the elements form a plurality of arrays.

15. The device as recited in claim 11 wherein said image is produced by a plurality of arrays, each array comprising one or more of said elements such that the first plates in each array are parallel to a first line first line that joins one said crystal to said point, with said first line being different for each array and with no two said first lines parallel to each other.

16. The device as recited in claim 15 wherein said first plates in each array are parallel to a second line that is perpendicular to the array's first line, with no two said second lines parallel to each other.

17. The device as recited in claim 16 wherein no more than two of said first lines of said arrays are co-planar.

18. The device as recited in claim 11 wherein said diffracting crystals are so positioned as to employ Laue diffraction in diffracting radiation from said sources.

19. The device as recited in claim 11 wherein said diffracting crystals are so positioned as to employ Bragg diffraction in diffracting radiation from said sources.

20. The device as recited in claim 11 wherein said crystals act as focusing crystals with said elements having a spatial resolution 20 arcsec FWHM.

* * * * *